United States Patent
Housman

(10) Patent No.: US 11,219,442 B2
(45) Date of Patent: Jan. 11, 2022

(54) EXPANDING KNOTLESS SUTURE ANCHOR

(71) Applicant: Smith & Nephew, Inc., Memphis, TN (US)

(72) Inventor: Mark E. Housman, North Attleboro, MA (US)

(73) Assignee: Smith & Nephew, Inc., Memphis, TN (US)

(*) Notice: Subject to any disclaimer, the term of this patent is extended or adjusted under 35 U.S.C. 154(b) by 134 days.

(21) Appl. No.: 16/096,325

(22) PCT Filed: Mar. 21, 2017

(86) PCT No.: PCT/US2017/023357
§ 371 (c)(1),
(2) Date: Oct. 25, 2018

(87) PCT Pub. No.: WO2017/192214
PCT Pub. Date: Nov. 9, 2017

(65) Prior Publication Data
US 2019/0125332 A1 May 2, 2019

Related U.S. Application Data

(60) Provisional application No. 62/331,089, filed on May 3, 2016.

(51) Int. Cl.
*A61B 17/04* (2006.01)

(52) U.S. Cl.
CPC .. *A61B 17/0401* (2013.01); *A61B 2017/0409* (2013.01); *A61B 2017/0412* (2013.01);
(Continued)

(58) Field of Classification Search
CPC ........ A61B 17/0401; A61B 2017/0412; A61B 17/7076; A61B 17/7091;
(Continued)

(56) References Cited

U.S. PATENT DOCUMENTS 5,702,397 A * 12/1997 Goble ................ A61B 17/0401
606/232
7,713,285 B1  5/2010 Stone et al.
(Continued)

FOREIGN PATENT DOCUMENTS

WO    9730649 A1    8/1997
WO    0044293 A1    8/2000

OTHER PUBLICATIONS

International Search Report and Written Opinion from related PCT Application No. PCT/US2017/023357 dated Jun. 6, 2017.

*Primary Examiner* — Melanie R Tyson
*Assistant Examiner* — Mohammed S Adam
(74) *Attorney, Agent, or Firm* — Burns & Levinson LLP; Joseph M. Maraia

(57) ABSTRACT

A suture anchoring system having an implant body that defines a bore space extending longitudinally about a central axis from a proximal end to a distal end of the implant body. A tapering interference portion is provided on an interior surface of the implant body and extends into the bore space, the taper being toward the central axis of the implant body bore space from the proximal end to the distal end of the implant body. An anchor has a threaded anchor portion extending therefrom and defines a threaded bore, where the extended threaded anchor portion configured to be received in the bore space of the implant body. A slot is defined in the threaded anchor portion, the slot configured to receive the interference portion of the implant body; and a threaded plug is configured to be received in the threaded bore of the anchor.

17 Claims, 16 Drawing Sheets

(52) U.S. Cl.
CPC ............... *A61B 2017/0414* (2013.01); *A61B 2017/0424* (2013.01); *A61B 2017/0425* (2013.01); *A61B 2017/0432* (2013.01); *A61B 2017/0433* (2013.01); *A61B 2017/0438* (2013.01); *A61B 2017/0445* (2013.01)

(58) Field of Classification Search
CPC .... A61B 2017/0445; A61B 2017/0438; A61B 2017/042; A61B 2017/0422; A61B 2017/0427

See application file for complete search history.

(56) References Cited

U.S. PATENT DOCUMENTS

| | | | |
|---|---|---|---|
| 10,149,751 B2 * | 12/2018 | Ticker ................ | A61B 17/0485 |
| 2009/0187216 A1 * | 7/2009 | Schmieding ....... | A61B 17/0401 606/232 |
| 2011/0166600 A1 * | 7/2011 | Lamborne .......... | A61B 17/7061 606/249 |
| 2016/0113643 A1 * | 4/2016 | Diduch ................ | A61F 2/0805 606/232 |

* cited by examiner

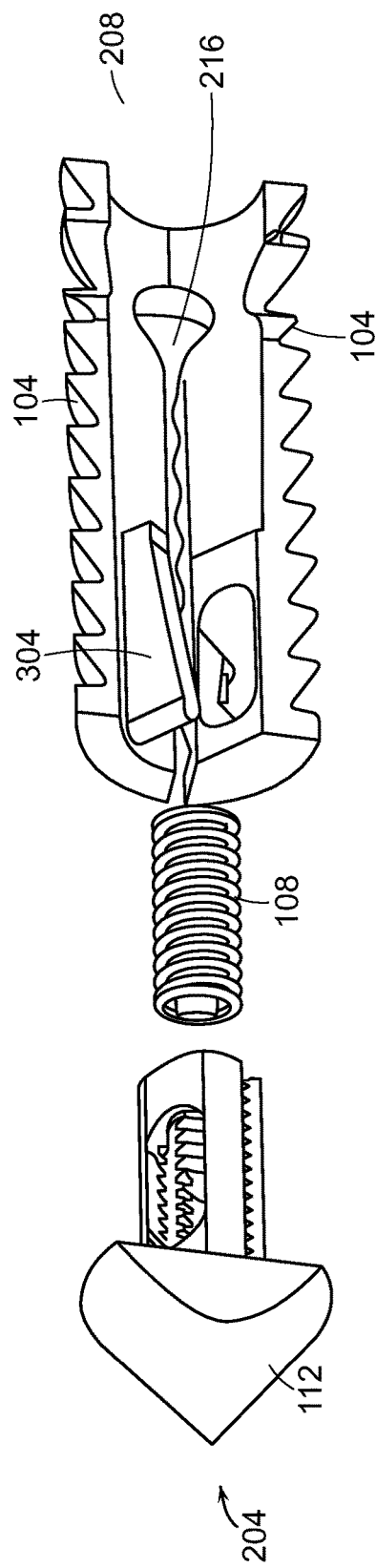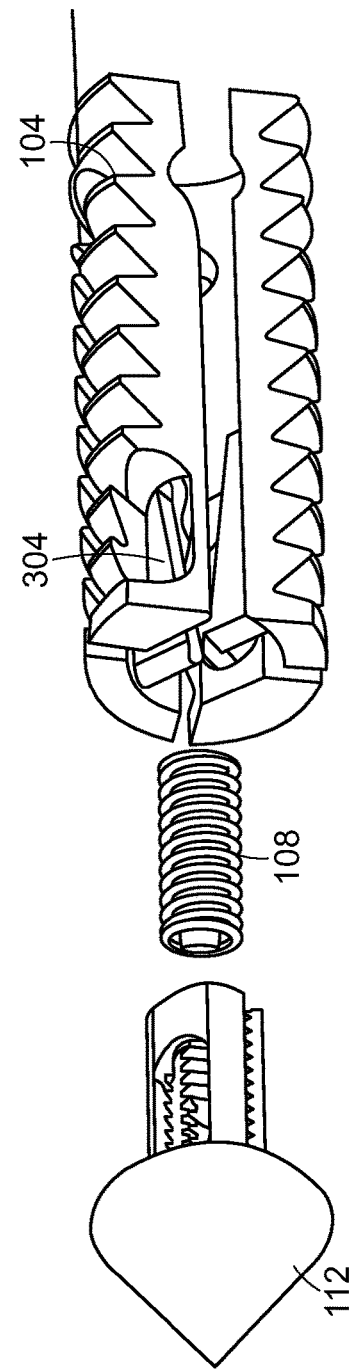

EXPANDING KNOTLESS SUTURE ANCHOR

CROSS REFERENCE TO RELATED APPLICATIONS

This application is the U.S. National Phase entry under 35 U.S.C. § 371 of International Application No. PCT/US2017/023357, filed Mar. 21, 2017, entitled EXPANDING KNOTLESS SUTURE ANCHOR, which claims priority to and the benefit of U.S. Provisional Application No. 62/331,089, filed May 3, 2016, entitled EXPANDING KNOTLESS SUTURE ANCHOR.

BACKGROUND OF THE INVENTION

Current pound-in no-hole preparation anchors do not provide sufficient fixation (pullout) strength.

BRIEF SUMMARY OF THE INVENTION

A suture anchoring system comprises an implant body defining a bore space extending longitudinally about a central axis from a proximal end to a distal end of the implant body. An interference portion is provided on an interior surface of the implant body and extends into the bore space, the interference portion configured to taper toward the central axis of the implant body bore space from the proximal end to the distal end of the implant body. An anchor having a threaded anchor portion extending therefrom and defining a threaded bore, the extended threaded anchor portion configured to be received in the bore space of the implant body, is provided. A slot is defined in the threaded anchor portion, the slot configured to receive the interference portion of the implant body and a threaded plug is configured to be received in the threaded bore of the anchor.

In another version, a suture anchoring device, comprises an implant body defining a body bore space extending longitudinally about a central axis from a proximal end to a distal end of the implant body. An interference portion is provided on an interior surface of the implant body and extends into the body bore space. An anchor having a head portion and an extension portion extending therefrom and defining an extension bore space therein, the extension portion configured to be received in the body bore space is provided and a slot is defined by the extension portion, the slot configured to receive the interference portion of the implant body. A plug is configured to be received in the bore space of the extension portion.

BRIEF DESCRIPTION OF THE DRAWINGS

Various aspects of at least one embodiment of the present invention are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention. In the figures:

FIGS. 2-1 and 2-2 are partial, cutaway, exploded views of an anchoring system;

FIGS. 3-1 to 3-2 represent an inner surface of an implant body including a pair of opposed ramps;

FIGS. 4-1 and 4-2 are orthogonal cross-sectional views through the implant body;

FIGS. 5-1 and 5-2 represent, respectively, views into the implant body from the proximal and distal ends;

FIGS. 6-1 to 6-5 represent a conical anchor head portion and an extension portion of an anchor;

FIGS. 7-1 and 7-2 represent an exploded view of the device; and

FIGS. 8-1 and 8-2 are depictions of the device in two orthogonal cross sections.

DETAILED DESCRIPTION

Figure 1:
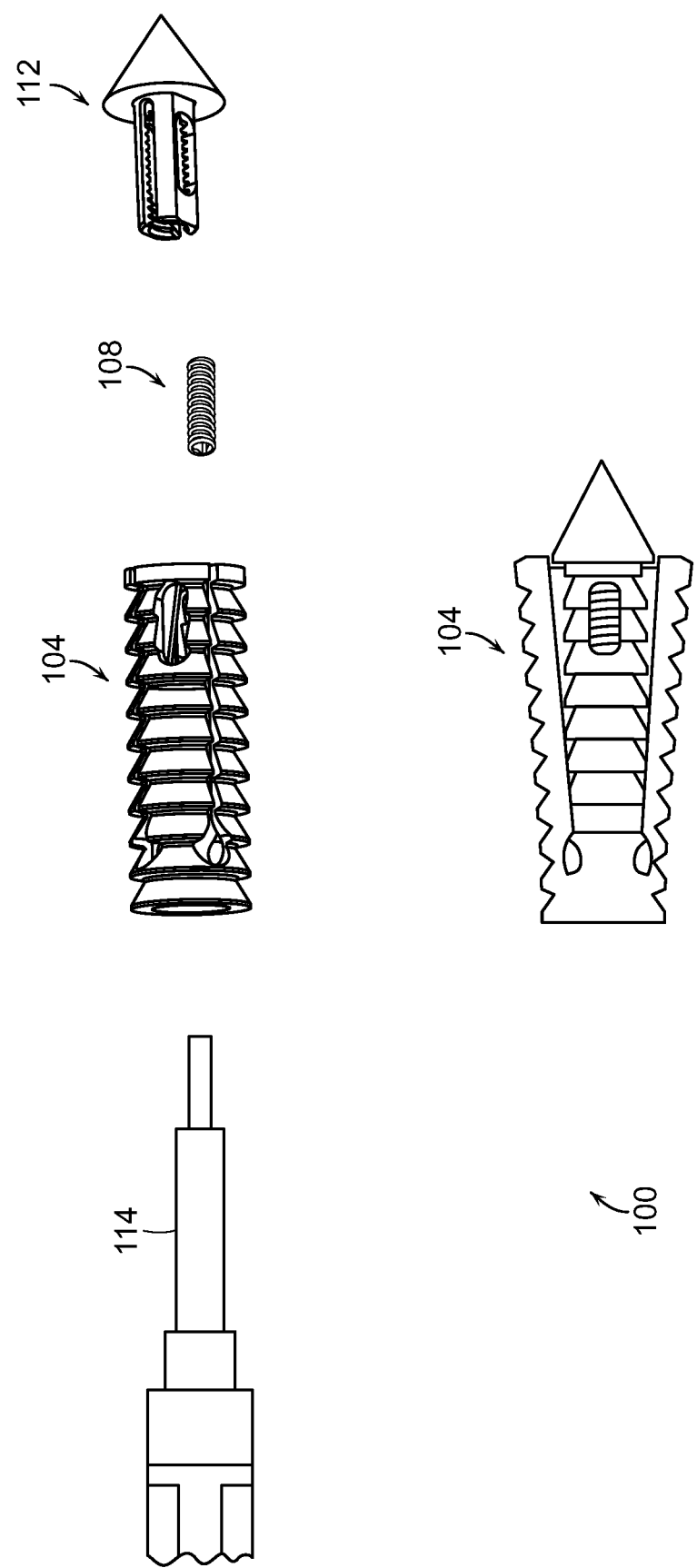
FIGS. 1-1 and 1-2 represent a suture anchoring system in accordance with one embodiment.

In the following detailed description, numerous specific details are set forth in order to provide a thorough understanding of the embodiments of the present invention. It will be understood by those of ordinary skill in the art that these embodiments of the present invention may be practiced without some of these specific details. In other instances, well-known methods, procedures, components and structures may not have been described in detail so as not to obscure the embodiments of the present invention.

Prior to explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description only and should not be regarded as limiting.

It is appreciated that certain features, are, for clarity, described in the context of separate embodiments but may also be provided in combination in a single embodiment. Conversely, various features are, for brevity, described in the context of a single embodiment but may also be provided separately or in any suitable sub-combination.

Embodiments of the present invention are directed to an expanding, knotless suture anchor that does not require hole preparation prior to insertion. It provides active suture retention and superior fixation strength via anchor expansion.

Figures 1, 2:
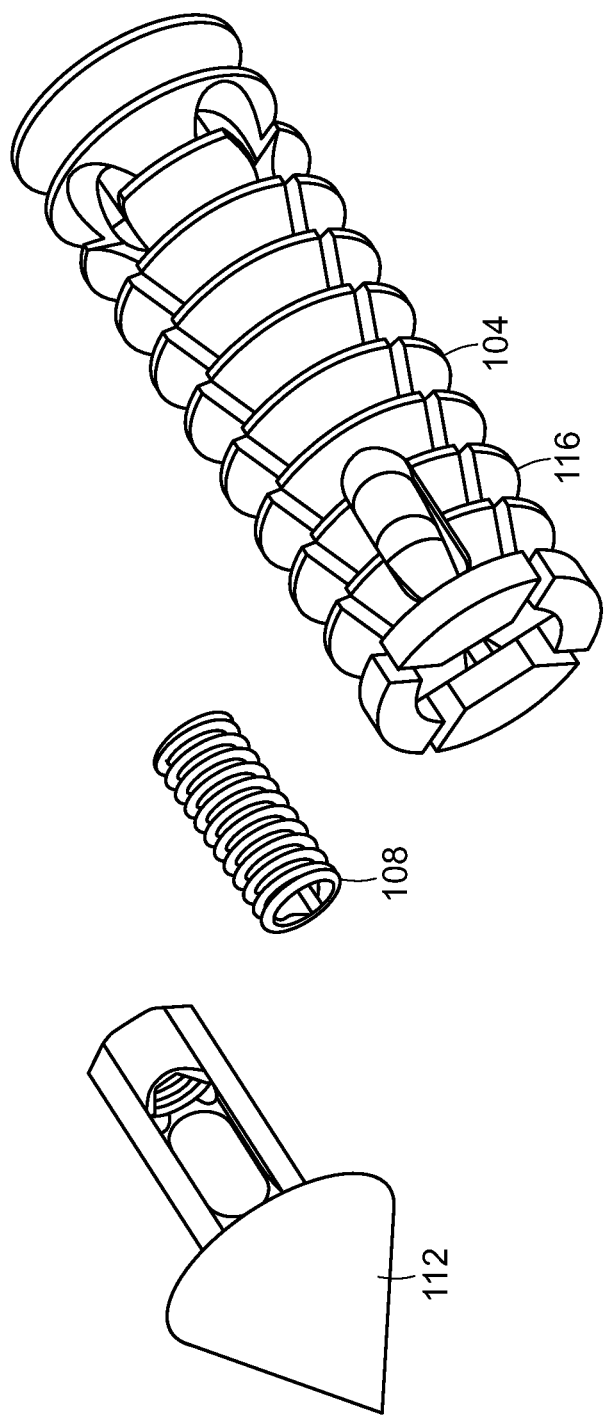
Figures 1, 2:
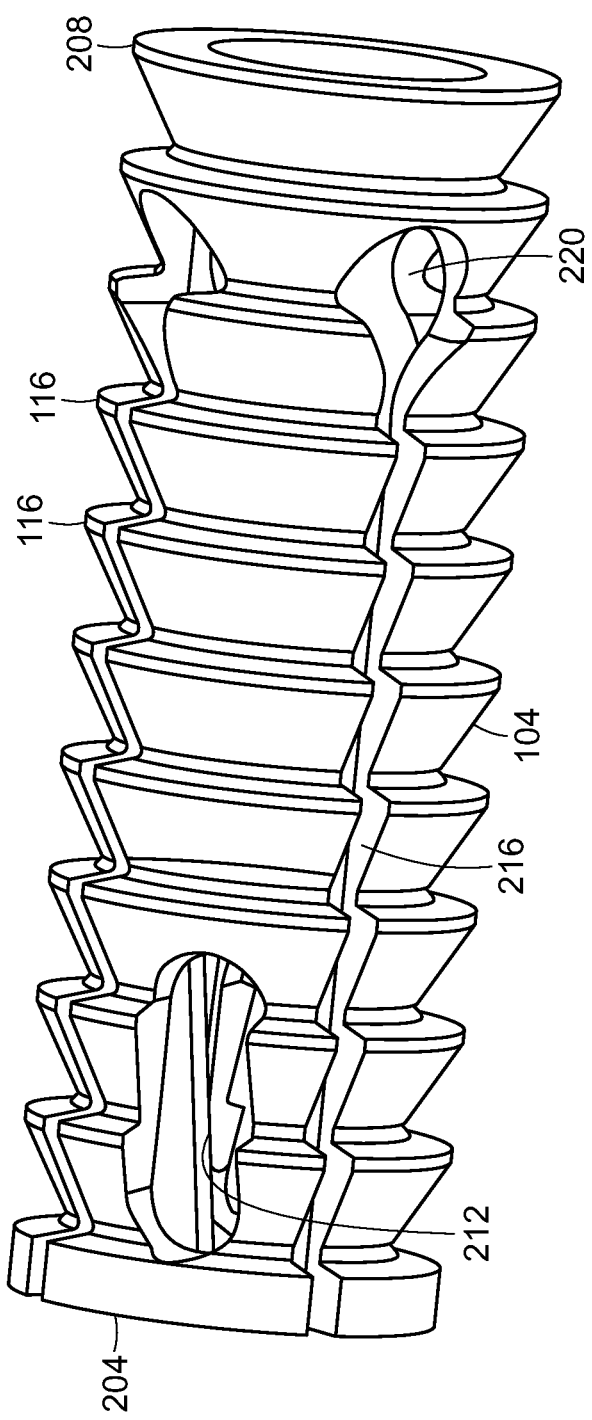
Figure 2:
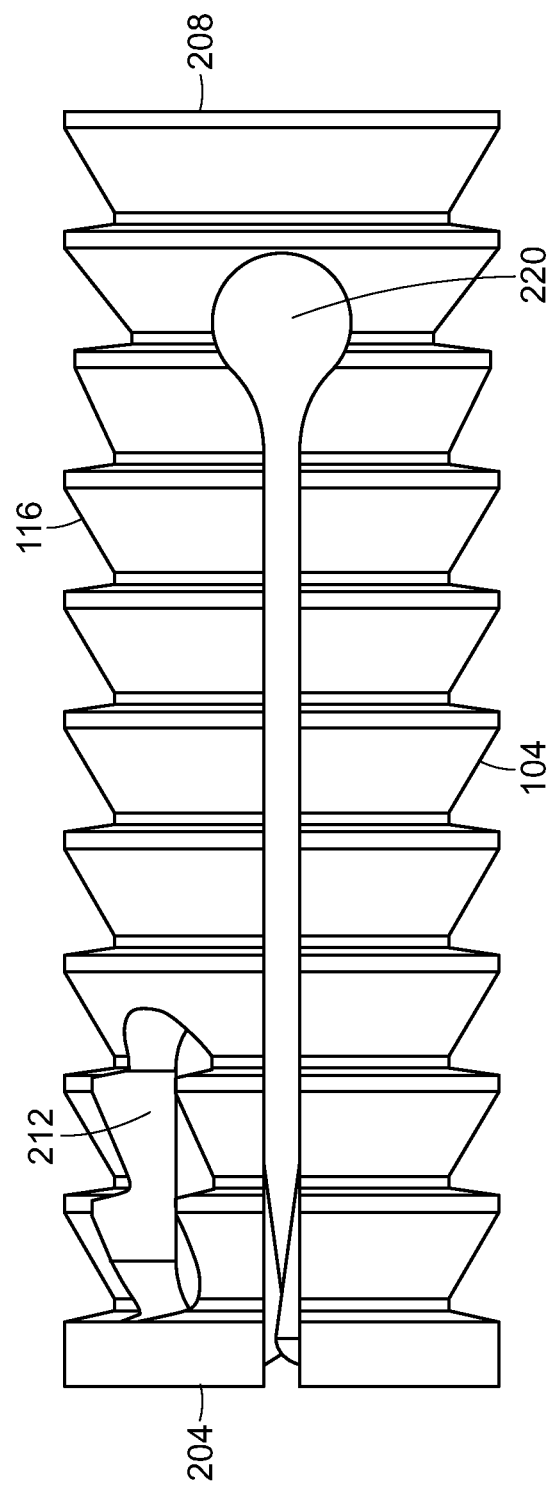

Referring now to FIGS. 1-1 through 1-2, a suture anchoring system 100 in accordance with one embodiment of the present invention is shown. As seen in FIG. 1-1, the system 100, in an unassembled state, shown in the upper portion of the figure, includes an implant body 104, a plug 108, an anchor 112 and an insertion tool 114. The implant body 104 may have a plurality of barbs 116 on its outer surface.

The implant body 104, referring to FIGS. 2-1 and 2-2 which are partial cutaway views of the exploded anchoring system 100, includes a distal end 204 and a proximal end 208, for reference, at least one body eyelet 212 defined in the outer surface and at least one relief slot 216 having a stress release radius or radial portion 220. As above, the outer surface of the implant body 104 may include one or more barbed structures or may be smooth but with a circumference that decreases from the proximal end 208 to the distal end 204, i.e., a conical shape.

Figures 1, 3:
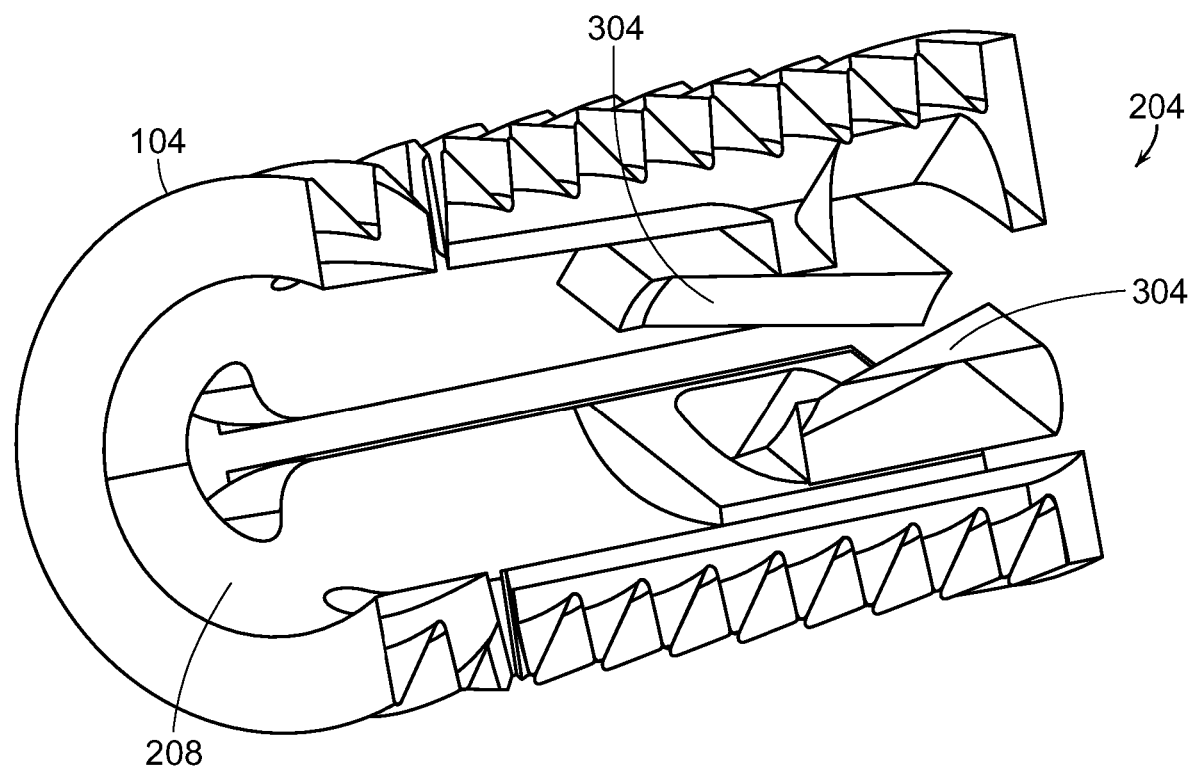
Figures 2, 3:
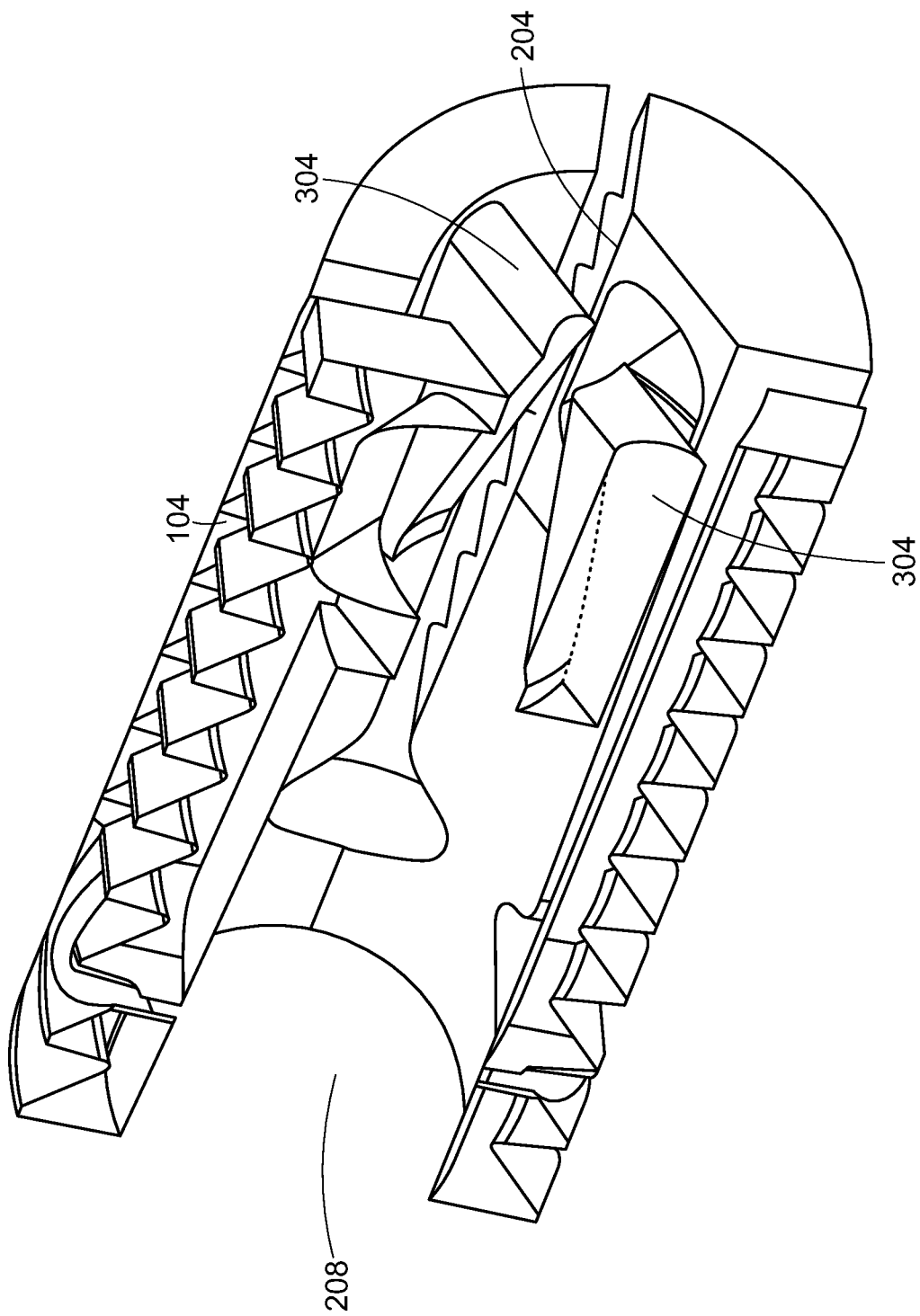

An inner surface of the implant body 104 includes a pair of opposed ramps 304 disposed toward the distal end 204 of the implant body 104, as shown in FIGS. 3-1 and 3-2. The function of the ramps 304 will be described in more detail below.

Figures 1, 4:
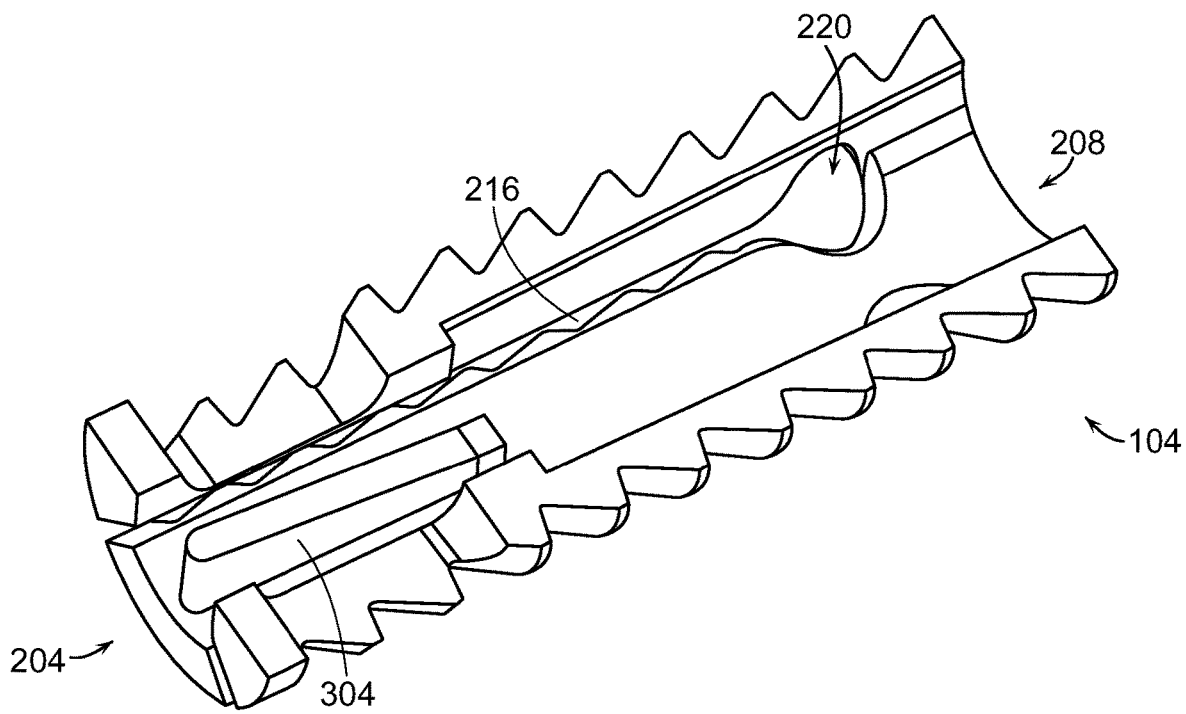
Figures 2, 4:
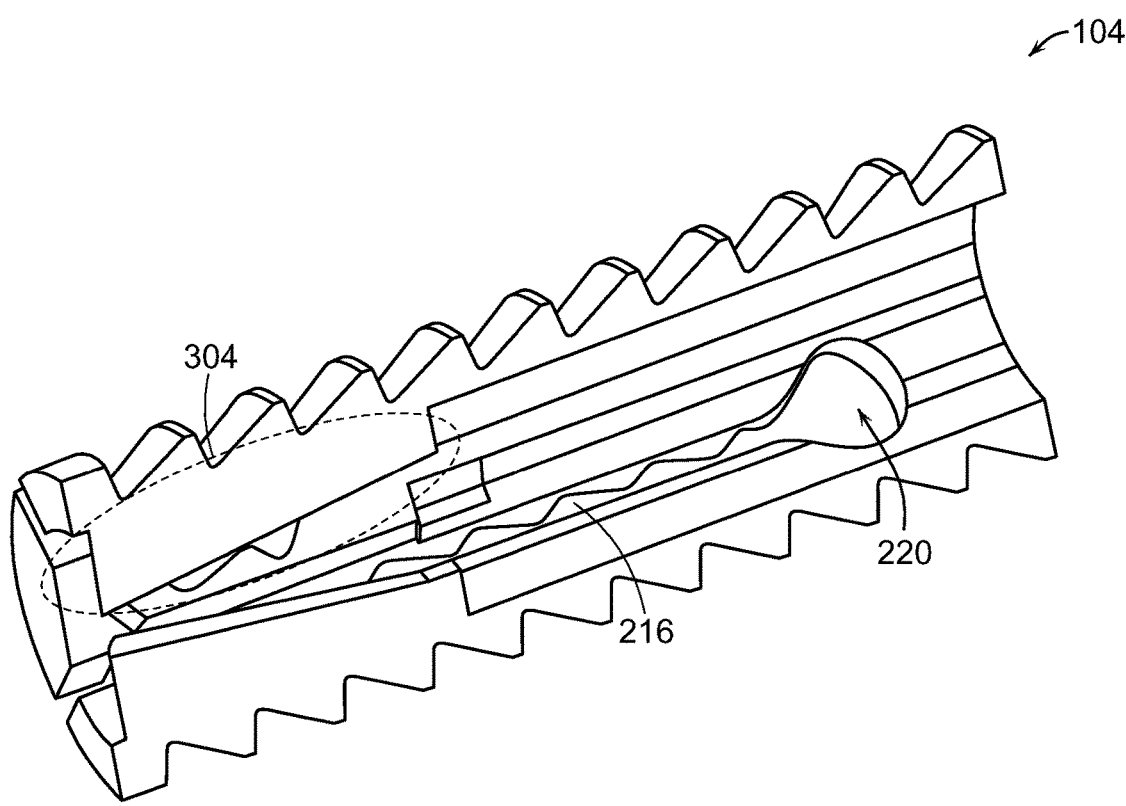

As shown in FIGS. 4-1 and 4-2, two orthogonal cross-sectional views through the implant body 104 are presented, respectively, and one embodiment of the shape and form of the interference ramp 304 can be seen and understood. The interference ramp 304 is tapered toward the midline of the implant body 104, i.e., into the defined inner space, and increases from the proximal end 208 to the distal end 204.

To enable radial expansion of the implant body 104, further explained below, each of the plurality of relief slots 216 extends from the distal end 204 of the implant body 104 terminating in the stress release radius 220 located toward the proximal end 208 of the implant body 104. The relief slots 216 and stress release radius 220 allow the implant body 104 to expand radially outward with minimal resistance and without sustaining structural damage, e.g., cracking.

Figures 1, 5:
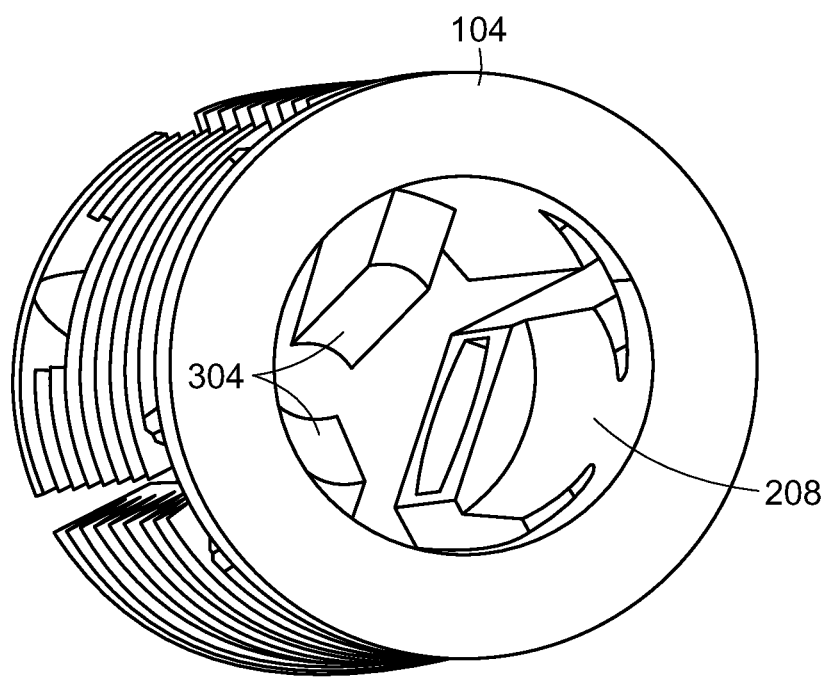
Figures 2, 5:
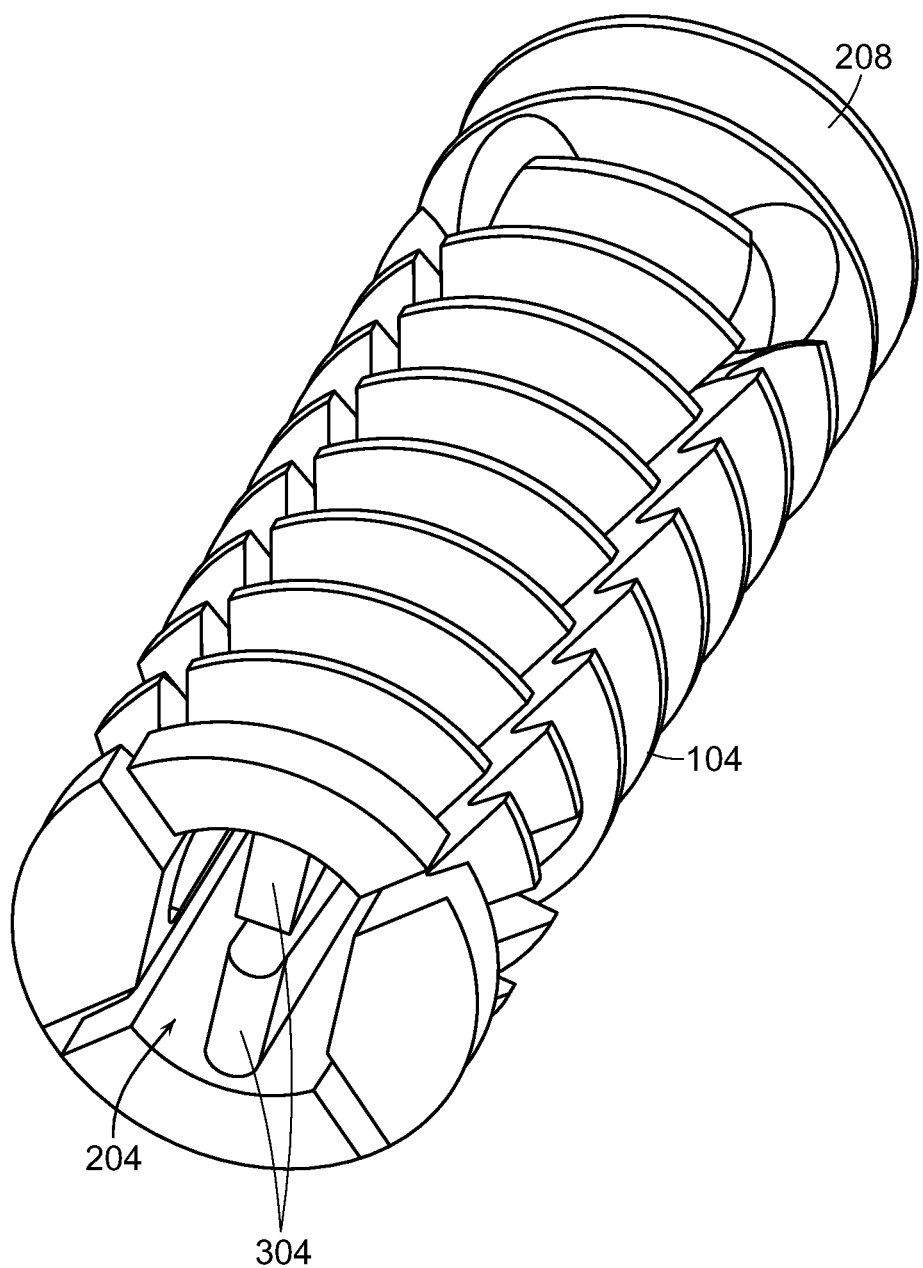

FIGS. 5-1 and 5-2 represent, respectively, views into the implant body 104 from the proximal and distal ends, respectively.

Figures 1, 6:
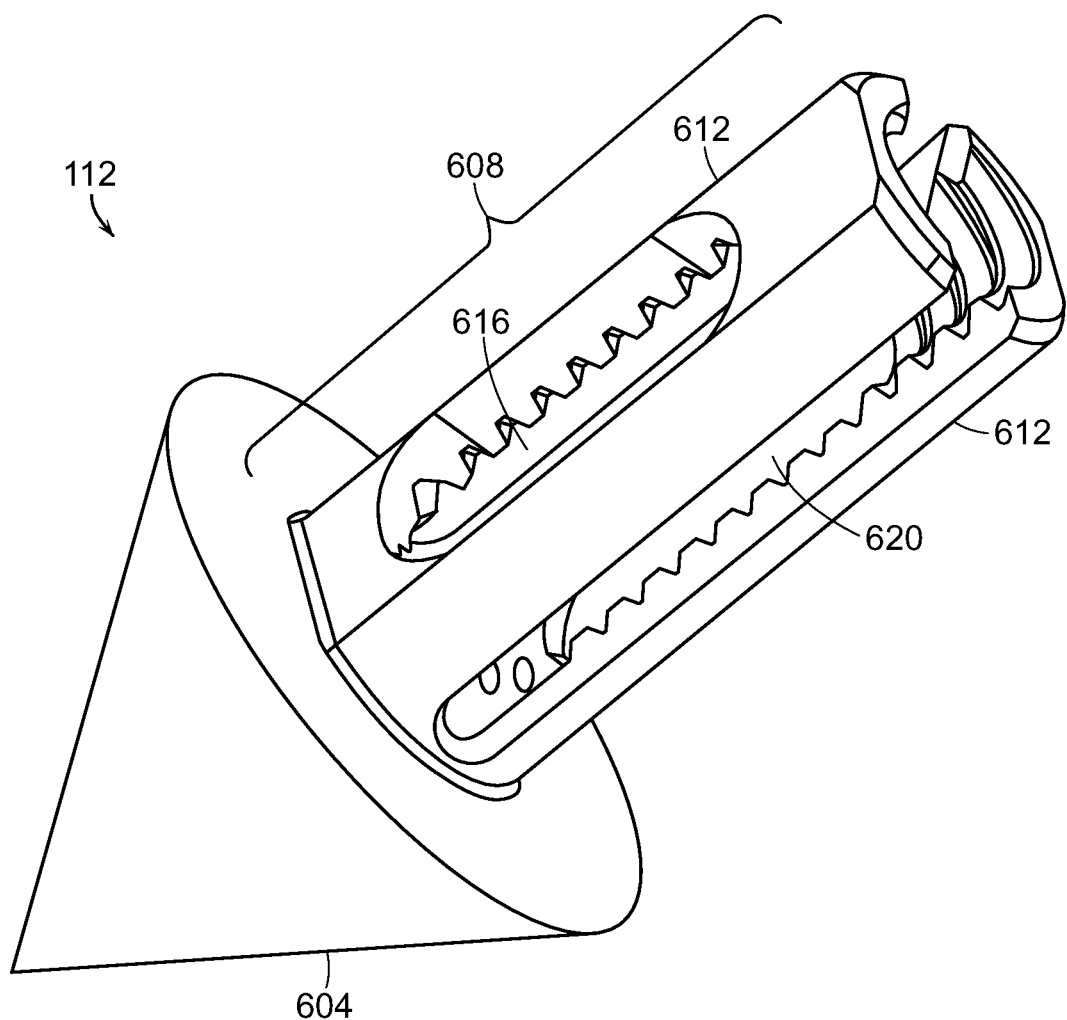
Figures 2, 6:
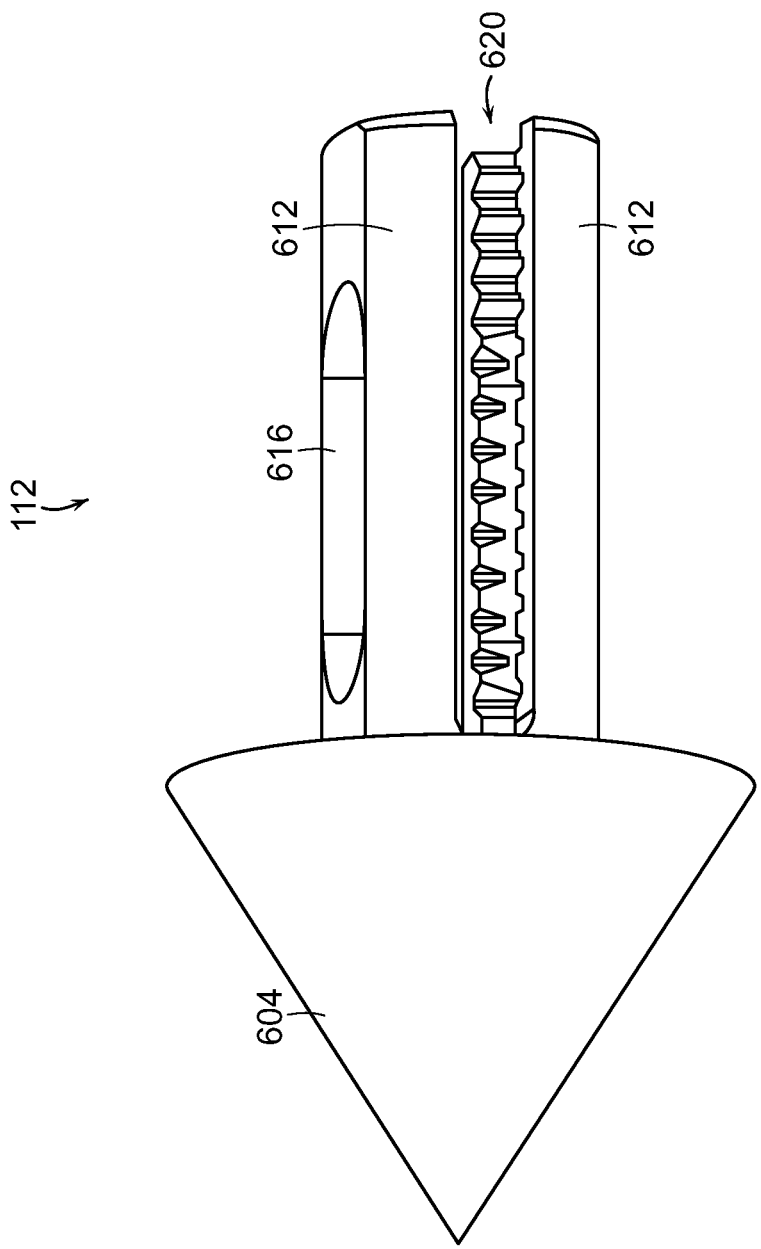
Figures 3, 6:
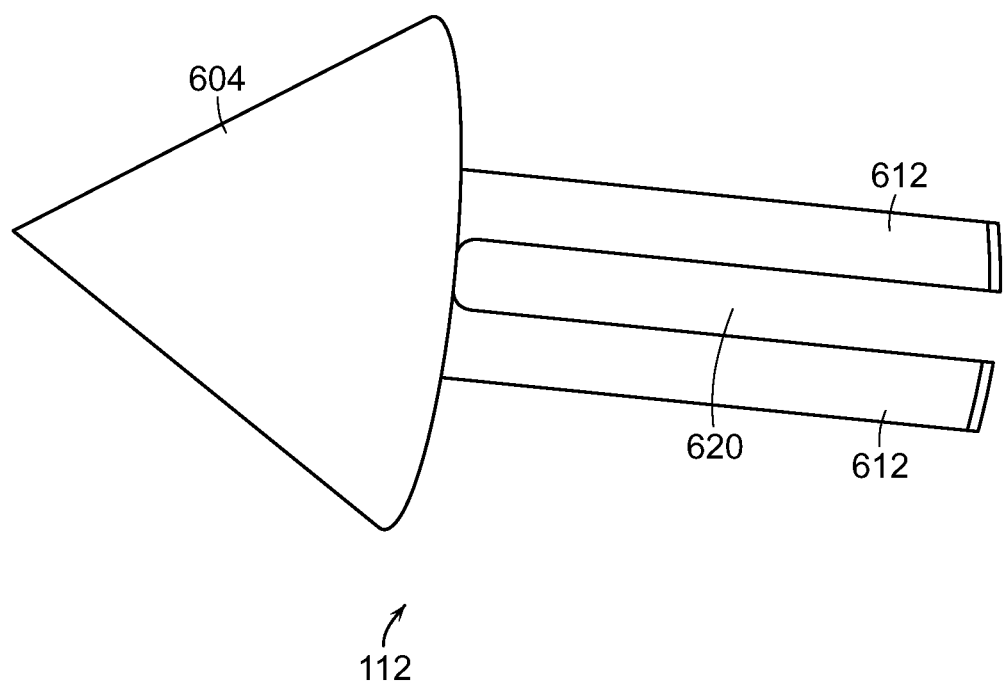
Figures 4, 6:
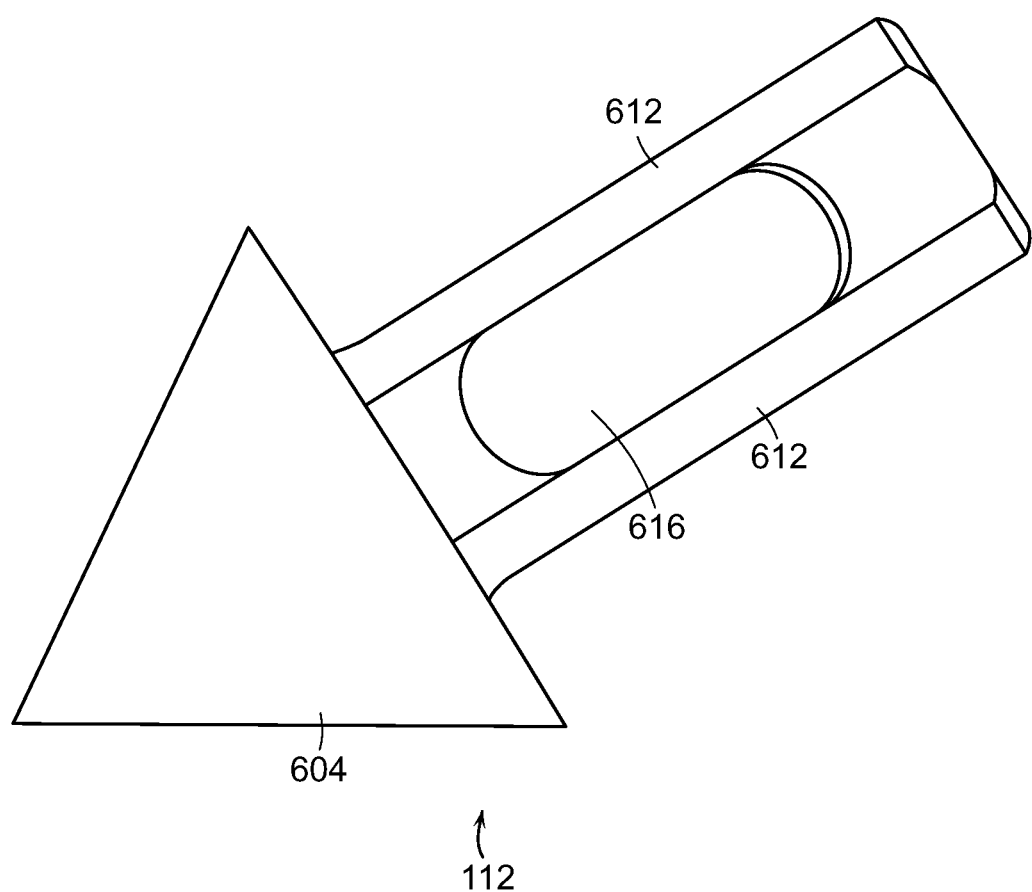
Figures 5, 6:
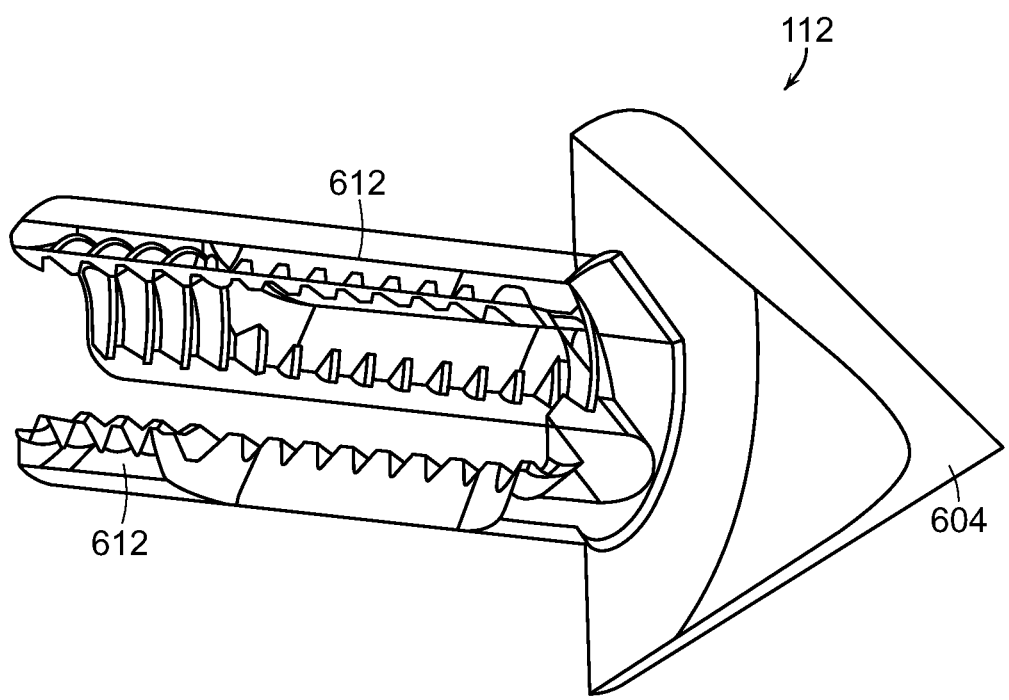

The anchor 112, as shown in FIGS. 6-1 to 6-5, includes a conical anchor head portion 604 and an extension portion 608. In one embodiment, the extension portion 608 comprises two parallel prongs 612 that extend from the anchor head portion 604. An anchor eyelet 616 for receiving a suture is defined in each of the prongs 612 of the extension portion 608. In addition, an inner surface defined by the prongs 612 of the extension portion 608 may be threaded to engage with a threaded outer surface of the plug 108. An interference slot is defined between the two prongs 612 to allow interaction between the plug 108 and the interference ramps 304 on the implant body 104 interior.

Referring to FIGS. 7-1 and 7-2, an exploded view of the device 100, generally, the anchor 112 is provided in the distal end 204 of the implant body 104 and the plug 108 is provided in the proximal portion of the implant body 104. The anchor 112 is oriented such that the ramps 304 are provided in the slots of the anchor 112. As a result, the body eyelets 212 of the implant body 104 and the anchor eyelets 616 of the anchor 112 align with one another. The plug 108 is urged distally through the implant body 104 to engage with the threads of the anchor 112. The insertion tool 114 is used to screw the plug 108 into the anchor 112.

Figures 1, 8:
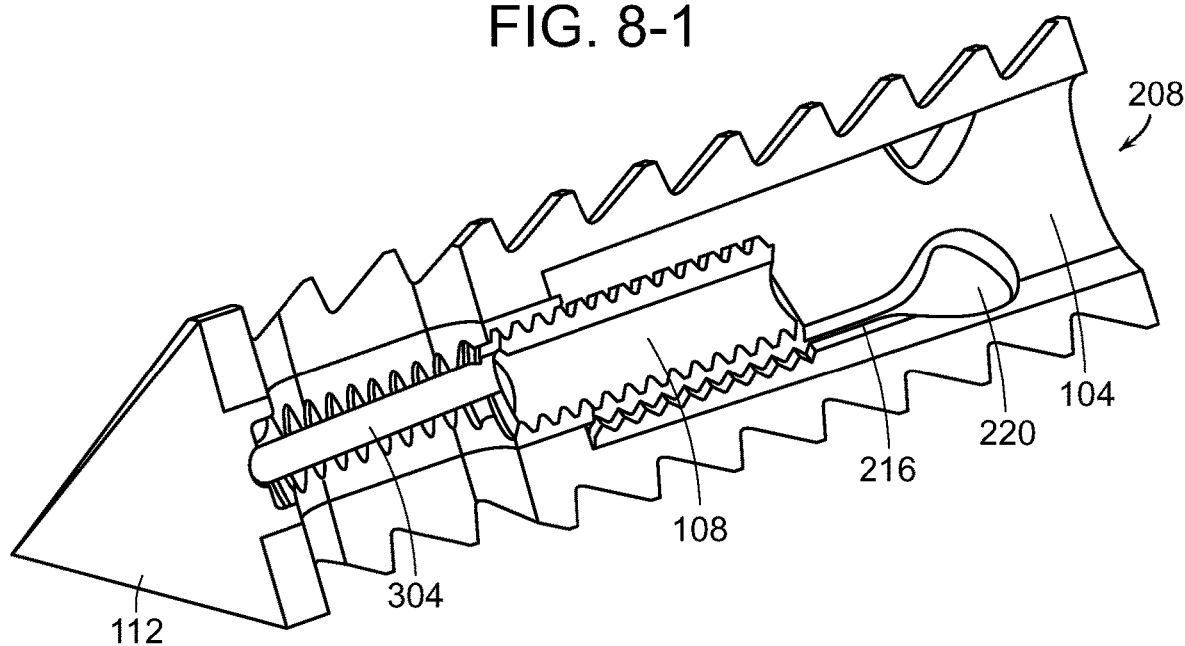
Figures 2, 8:
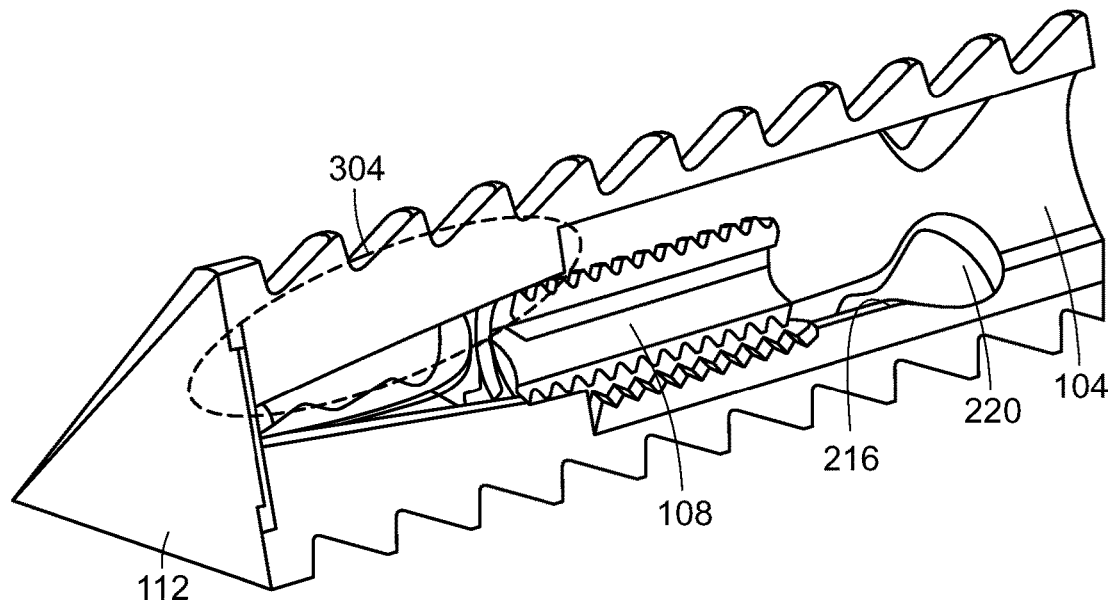

An arrangement of the components is shown in FIGS. 8-1 and 8-2, which are depictions of the device 100 in two orthogonal cross sections, one through the body and anchor eyelets 212, 616 and one perpendicular to the body and anchor eyelets 212, 616, respectively. The plug 108 is shown in its pre-deployed position. In this position, the plug 108 still connects the implant assembly to an inserter (not shown). After implantation in bone, the plug 108 would be moved distally, releasing the implant assembly from the driver (not shown), expanding the anchor 112 through interaction with the interference ramp 304 and also impinging/retaining a suture threaded through the anchor and implant body eyelets 212, 616.

In operation, the distally moving plug 108 collides with the interference ramps 304 and causes the distal end 204 of the implant body 104 to flare out. Interference slots 620 are defined in the anchor 112 and allow the plug 108 to interface with the ramps 304. The expansion of the implant body 104 is facilitated by the relief slots 216 that allow the implant body 104 to expand radially with minimal force.

In one embodiment, the anchor 112 may be made of a material, e.g., a metal, that is harder than the implant body 104 which is made of a softer material, e.g., a plastic.

Advantageously, the movement of the plug 108 from the proximal to distal ends within the implant body 104 releases the implant from the inserter, expands the implant body 104 and entraps the suture.

In one embodiment, a barbed exterior is described, however, a multitude of exterior geometries could be utilized. Alternative fixation features may be implemented, as known to those of ordinary skill in the art, such as CAFT or flexible wings. Further, while two interference ramps 304 are shown as an example, any number of ramps 304 could be utilized. The current device is described with reference to a threaded plug 108, however, a linear interference plug 108 could be utilized where the plug is without threads but sized to provide a slip fit/light interference interaction when it is slid linearly, from proximal to distal, within the assembly.

It is to be understood that the detailed descriptions of the embodiments of the present invention are provided by way of example only and are not intended to limit the scope of the invention. Features and/or steps described with respect to one embodiment may be used with other embodiments and not all embodiments of the invention have all of the features and/or steps shown in a particular figure or described with respect to one of the embodiments. Variations of embodiments described will occur to persons of skill in the art.

Although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the appended claims.

What is claimed is:

1. A suture anchoring device, comprising:
   a radially expandable implant body defining a body bore space extending longitudinally about a central axis from a proximal end to a distal end of the implant body;
   at least one relief slot defined in the implant body, each at least one relief slot extending from the distal end of the implant body, and each at least one relief slot configured to allow the distal end of the implant body to radially expand relative to the proximal end of the implant body;
   an interference portion provided on an interior surface of the distal end of the implant body and extending into the body bore space;
   an anchor having a head portion and an extension portion extending therefrom such that the extension portion does not move relative to the head portion, the extension portion defining an extension bore space therein, the extension portion configured to be received in the body bore space such that the distal end of the implant body abuts the head portion of the anchor and the extension portion is prevented from extending through the at least one relief slot;
   a slot defined by the extension portion, the slot configured to receive the interference portion of the implant body; and
   a plug configured to be received in the extension bore space;
   wherein the head portion of the anchor defines the distalmost end of the suture anchoring device.

2. The suture anchoring device of claim 1, wherein:
the interference portion is configured to taper toward the central axis of the implant body bore space from the proximal end to the distal end of the implant body.

3. The suture anchoring device of claim 1, wherein the interference portion comprises a ramped surface.

4. The suture anchoring device of claim 1, wherein the interference portion comprises a plurality of ramped surfaces.

5. The suture anchoring device of claim 1, wherein:
a plurality of threads is defined on a portion of an inner surface of the extension portion of the anchor.

6. The suture anchoring device of claim 5, wherein:
the plug comprises a threaded outer surface configured to interact with the threads of the inner surface of the extension portion of the anchor; and
wherein the plug is configured to entrap a suture extending through an eyelet defined by the extension portion.

7. The suture anchoring device of claim 1, wherein:
the anchor head portion comprises a first material; and
the implant body comprises a second material,
wherein the first material is harder than the second material.

8. The suture anchoring device of claim 7, wherein the first material comprises a metal.

9. The suture anchoring device of claim 7, wherein the second material comprises a plastic.

10. The suture anchoring device of claim 1, further comprising at least one eyelet defined in the anchor.

11. The suture anchoring device of claim 1, wherein the extension portion of the anchor comprises:
first and second prongs extending parallel to one another from a proximal surface of the anchor head portion.

12. The suture anchoring device of claim 11, wherein first and second eyelets are defined in the first and second prongs, respectively.

13. The suture anchoring device of claim 11, wherein the slot is defined between the first and second prongs.

14. The suture anchoring device of claim 1, wherein each at least one relief slot comprises a stress attenuation radius portion that is distal to and spaced apart from the proximal end of the implant body.

15. The suture anchoring device of claim 1, further comprising a plurality of barbs disposed on an outer surface of the implant body.

16. The suture anchoring device of claim 1, wherein an outer surface of the implant body comprises a tapered geometry where a proximal diameter is larger than a distal diameter.

17. The suture anchoring device of claim 1, further comprising a plurality of interference portions.

* * * * *